(12) United States Patent
Kleider et al.

(10) Patent No.: US 11,378,573 B2
(45) Date of Patent: Jul. 5, 2022

(54) CALIBRATION FOR MULTI-COMPONENT ASSAYS

(71) Applicant: Roche Diagnostics Operations, Inc., Indianapolis, IN (US)

(72) Inventors: Wilhelm Kleider, Uffing am Staffelsee (DE); Hans-Dieter Kraemer, Penzberg (DE); Peter Sluka, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 484 days.

(21) Appl. No.: 14/956,733

(22) Filed: Dec. 2, 2015

(65) Prior Publication Data
US 2016/0084861 A1 Mar. 24, 2016

Related U.S. Application Data

(63) Continuation of application No. PCT/EP2014/061571, filed on Jun. 4, 2014.

(30) Foreign Application Priority Data

Jun. 7, 2013 (EP) .................... 13171044

(51) Int. Cl.
*G01N 33/68* (2006.01)
*G01N 33/53* (2006.01)
*G01N 33/50* (2006.01)
*G01N 33/543* (2006.01)
*G01N 35/00* (2006.01)
*G01N 21/59* (2006.01)
*G01N 27/26* (2006.01)

(52) U.S. Cl.
CPC ......... *G01N 33/5306* (2013.01); *G01N 33/50* (2013.01); *G01N 33/5308* (2013.01); *G01N 33/54313* (2013.01); *G01N 33/68* (2013.01); *G01N 33/6893* (2013.01); *G01N 35/00693* (2013.01); *G01N 21/59* (2013.01); *G01N 27/26* (2013.01); *G01N 2035/00702* (2013.01); *G01N 2201/127* (2013.01); *G01N 2333/4737* (2013.01)

(58) Field of Classification Search
CPC .......... G01N 33/5306; G01N 33/5308; G01N 33/54313; G01N 33/68
See application file for complete search history.

(56) References Cited

U.S. PATENT DOCUMENTS 6,277,584 B1 8/2001 Chu et al.

2003/0235817 A1* 12/2003 Bartkowiak ....... A61B 5/14532
435/5
2011/0223066 A1 9/2011 Yamazaki et al.
2011/0236996 A1* 9/2011 Nakayama ......... G01N 33/6893
436/501

FOREIGN PATENT DOCUMENTS

| EP | 0898169 B1 | 2/2002 |
|---|---|---|
| EP | 0790500 B1 | 6/2002 |
| EP | 2034313 A1 | 3/2009 |
| EP | 1801590 B1 | 7/2010 |
| EP | 2357475 A1 | 8/2011 |

OTHER PUBLICATIONS

Mida et al., Validation of homogeneous assays for HDL-cholesterol using fresh samples from healthy and diseased subjects, Atherosclerosis 233 (2014) 253-259 (Year: 2014).*
Him et al., Hitachi 917 operator manual, v 2.1, 406 pages, retrieved from http://www.frankshospitalworkshop.com/equipment/documents/automated_analyzer/user_manuals/Hitachi%20917%20Analyzer%20-%20User%20manual.pdf on Sep. 6, 2018 (Year: 1997).*
Dictionary.com definition of operable retrieved from https://www.dictionary.com/browse/operability on Sep. 6, 2018 7 pages (Year: 2018).*
International Search Report dated Aug. 20, 2014 in Application No. PCT/EP2014/061571, 4 pages.
Graphpad Software, Inc., Equation: Two phase decay, GraphPad Curve Fitting Guide, downloaded Apr. 24, 2015, 2 pages.
Lindmo, Tore et al., Immunometric assay by flow cytometry using mixtures of two particle types of different affinity, Journal of Immunological Methods, 1990, pp. 183-189, vol. 126.
Perez-Amodio, Soledad et al., Effects of the Ionic Environment, Charge, and Particle Surface Chemistry for Enhancing a Latex Homogeneous Immunoassay of C-Reactive Protein, Anal. Chem., 2001, pp. 3417-3425, vol. 73.

* cited by examiner

*Primary Examiner* — Gailene Gabel
(74) *Attorney, Agent, or Firm* — Stinson LLP (57) ABSTRACT

A method of analyzing a biological sample using an analyzer and an assay. The method comprises providing the assay for producing the signal. The assay has two or more predetermined number of components. Each of the predetermined components has a distinct relation between the intensive property and the signal. The method further comprises providing calibration samples with known values for the intensive property and measuring a calibration signal for each of the calibration samples. The method further comprises determining a calibration by fitting a calibration function to the calibration signal for each of the calibration samples and the known values for the intensive property. The calibration function is equivalent to a constant plus an exponential decay term for each of the predetermined number of components. The method further comprises measuring the signal of the sample using the analyzer and the assay, and calculating the intensive property using the calibration.

10 Claims, 4 Drawing Sheets

CALIBRATION FOR MULTI-COMPONENT ASSAYS

CROSS-REFERENCE TO RELATED APPLICATIONS

This application is a continuation of International Patent Application No. PCT/EP2014/061571, filed 4 Jun. 2014, the disclosure of which is hereby incorporated by reference in its entirety.

FIELD OF THE DISCLOSURE

The present disclosure relates to the measurement of intensive properties of a biological sample using an assay, in particular when the assay has at least two components.

BACKGROUND

The application of nonlinear functions as calibration models for diagnostic assays is standard. In particular, these models allow for significant enlargement of the dynamic range of an assay where the signal-to-concentration relation is nonlinear. However, there is a specific class of assays where different biochemical processes are used to obtain accurate and precise results throughout the dynamic range, measurement range. For these assays the conventional nonlinear models have demonstrated to be not up to the clinical needs. This has led to the use of spline models, which however have disadvantages as they cannot discriminate insofar between measurement and model error.

SUMMARY

It is against the above background that the embodiments of the present disclosure provide certain unobvious advantages and advancements over the prior art. In particular, the inventors have recognized a need for improvements in calibration for multi-component assays.

In accordance with one embodiment of the disclosure, a method of analyzing a biological sample using an analyzer and an assay is provided, wherein the analyzer is operable for measuring a signal indicative of an intensive property of an analyte in the biological sample, wherein the intensive property is a concentration of the analyte, wherein the analyzer comprises a photometric measurement module operable for measuring the signal, and wherein the signal is at least a portion of a photometric transmission spectra. The method further comprises: providing the assay, wherein the assay is operable to produce the signal, wherein the assay has a predetermined number of components wherein the predetermined number of components is two, wherein each of the predetermined number of components has a distinct relation between the intensive property and the signal, and wherein each of the predetermined number of components is a distinct assay. The method further comprises providing a set number of calibration samples with known values for the intensive property; measuring a calibration signal for each of the calibration samples using the analyzer and the assay; determining a calibration by fitting a calibration function to the calibration signal for each of the calibration samples and the known values for the intensive property, wherein the calibration function is equivalent to a constant plus an exponential decay term for each of the predetermined number of components; measuring the signal of the biological sample using the analyzer and the assay; and calculating the intensive property using the signal and the calibration.

In accordance with another embodiment of the disclosure, an automatic analyzer for analyzing a biological sample is provided, wherein the analyzer is operable for measuring a signal descriptive of an intensive property of an analyte in the biological sample using an assay, wherein the intensive property is a concentration of the analyte, wherein the analyzer comprises a photometric measurement module operable for measuring the signal, and wherein the signal is at least a portion of a photometric transmission spectra, wherein the automatic analyzer is operable to receive the assay, wherein the assay has a predetermined number of components, wherein the predetermined number of components is two, wherein each of the predetermined number of components has a distinct relation between the intensive property and the signal, wherein each of the predetermined number of components is a distinct assay, wherein the automatic analyzer comprises a memory for storing machine executable instructions, wherein the automatic analyzer comprises a processor for controlling the automatic analyzer, and wherein execution of the instructions causes the processor to: receive a calibration, wherein the calibration is defined by a calibration function equivalent to a constant plus an exponential decay for each of the predetermined components; add the assay to the biological sample using the automatic analyzer; measure the signal of the biological sample using the automatic analyzer; and calculate the physical property using the signal and the calibration.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The term "analyzer" refers to a device being operable to execute one or multiple analyses on biological samples such as blood, urine, saliva, or other sample types. An analyzer is operable to determine via various chemical, biological, physical, optical or other technical procedures a parameter of the sample or a component thereof, the parameter in the following being referred to as "measurement value." An analyzer is operable to measure said parameter of the sample or of at least one assay and return the obtained measurement value. The list of possible analysis results returned by the analyzer comprises, without limitation, concentrations of the assay in the sample, a digital (yes or no) result indicating the existence of the assay in the sample (corresponding to a concentration above the detection level), optical parameters, DNA or RNA sequences, data obtained from mass spectroscopy of proteins or metabolites and physical or chemical parameters of various type.

As will be appreciated by one skilled in the art, aspects of the present disclosure may be embodied as a apparatus, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A "computer-readable storage medium" as used herein encompasses any tangible storage medium that may store instructions that are executable by a processor of a computing device. The computer-readable storage medium may be referred to as a "computer-readable non-transitory storage medium." The computer-readable storage medium may also be referred to as a "tangible computer readable medium." In some embodiments, a computer-readable storage medium may also be able to store data that is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

"Computer memory" or "memory" is an example of a computer-readable storage medium. Computer memory is any memory that is directly accessible to a processor. "Computer storage" or "storage" is a further example of a computer-readable storage medium. Computer storage is any non-volatile computer-readable storage medium. In some embodiments computer storage may also be computer memory or vice versa.

A "processor" as used herein encompasses an electronic component that is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code or machine executable instructions may comprise machine executable instructions or a program that causes a processor to perform an aspect of the present disclosure. Computer executable code for carrying out operations for aspects of the present disclosure may be written in any combination of one or more programming languages, including an object oriented programming language such as Java, Smalltalk, C++ or the like, and conventional procedural programming languages, such as the "C" programming language or similar programming languages, and compiled into machine executable instructions. In some instances the computer executable code may be in the form of a high level language or in a pre-compiled form and be used in conjunction with an interpreter that generates the machine executable instructions on the fly.

The machine executable instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the disclosure. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart and/or block diagram block or blocks.

A "hardware interface" as used herein encompasses an interface that enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

In accordance with one embodiment of the disclosure, a method of analyzing a biological sample using an analyzer and an assay is provided. The analyzer is operable for measuring a signal indicative of an intensive property of an analyte in the biological sample. An intensive property is a physical property of the biological sample that is scale invariant. For example, the concentration of a particular molecule, compound, or substance is an intensive property. An intensive property may also be referred to as a bulk property, an intensive quantity, or an intensive variable.

The assay is added to the biological sample and then a measurement is performed using the analyzer. The assay reacts in some manner with the analyte and is also responsible for generating the signal. For instance, the analyzer may have a transmission photo spectrometer where the transmission of light through the biological sample is measured. The assay may react with the analyte in such a way that an intensive property can be determined by making specific transmission measurements of the biological sample. A biological sample as used herein encompasses a sample that comprises material generated by a biochemical process or a biological system. A biological system may in some cases include parts or products of a living organism or chemicals or materials derived, replicated, or copied from an organism. For instance, DNA or RNA may be copied by a PCR process although the material is not directly generated by an organism it was derived from a biological system or organism. The intensive property of the analyte may be a physical property of the biological sample that may be measured.

In accordance with one embodiment of the disclosure, the method comprises the step of providing the assay. The assay is operable to produce the signal. The assay has a predetermined number of components. That is to say the assay is a mixture of a predetermined number of components. The predetermined components is greater than or equal to 2. Each of the predetermined number of components has a distinct relation between the intensive property and the signal. In other words, the assay is made up of two or more distinct assays. These two assays are mixed together to form the assay and each of the individual components has a distinct relation between the intensive property and the signal. Since the individual components all react and contribute to the signal the calibration takes into account the contribution from each of the components.

In accordance with an embodiment of the disclosure, the method further comprises providing a set number or fixed number of calibration samples with known values for the intensive property. The method further comprises measuring a calibration signal for each of the calibration samples using the analyzer and the assay. That is to say the assay is added to each of the calibration samples and a calibration signal is measured for each one. The method further comprises the step of determining a calibration by fitting a calibration function to the calibration signal for each of the calibration samples and the known values for the intensive property. The calibration function is equivalent to a constant plus an exponential decay term for each of the predetermined number of components. The term equivalent is used here because the calibration function can be arranged in different ways algebraically.

The calibration function can be written in a variety of ways. An exponential decay function can be considered to have the form $(1-\text{Exp}(-p3*\text{conc}))$ or $\text{Exp}(-p3*\text{conc})$, wherein p3 is a constant or calibration parameter. If the assay has two components, then the calibration function may have the form:

$$f(\text{conc})=p1+p2*(1-\text{Exp}(-p3*\text{conc}))+p4*(1-\text{Exp}(-p5*\text{conc})), \quad (1)$$

where p1, p2, p3, p4, and p5 are constants that have their value adjusted to define the calibration. "f" is the value of the signal, for example, the concentration ("conc") of the analyte. "Exp" is the exponential function. Equation 1 can be algebraically re-arranged in a variety of ways. For example, the following equation is equivalent to the previous equation:

$$f(\text{conc})=K1-p2*\text{Exp}(-p3*\text{conc})-p4*\text{Exp}(-p5*\text{conc}), \quad (2)$$

where $K1=p1+p2+p4$.

In accordance with an embodiment of the disclosure, the method further comprises the step of measuring the signal of the biological sample using the analyzer and the assay. The method further comprises the step of calculating the intensive property using the signal and the calibration. This embodiment may be beneficial because when there is an assay with multiple components and they each contribute to the same signal the calibration may be performed using a smaller number of calibration samples.

The components of the assay each have a distinct relationship with the signal. Depending upon the measurement system and the particular assay this may have different relationships. The different components may have different chemical processes that are followed. For instance, there may be different changes in wavelengths, different changes in temperatures after the assay is changed, or different transmission properties. Different modes may be used for measuring the signal. Spectroscopic methods that rely on the transmission of light may be used. In other examples chemiluminescence may be used, and temperature or pH measurements may also be made. The method is also applicable to nuclear magnetic resonance or NMR methods.

In another embodiment, the set number is at least 2 times the predetermined number of components plus 1. Each exponential decay term has two calibration parameters. In this embodiment each predetermined number of components has one exponential decay term that corresponds to it. The exponential decay term may be written in different ways; however, each exponential decay term regardless of its form will have two calibration parameters. A calibration parameter is a constant that may be adjusted to adjust the calibration curve. If the set number is equal to the number of calibration parameters then a solution for the calibration function can be calculated. In some examples a larger number than 2 times the predetermined number of components plus 1 is also used. In this case a larger number of calibration samples have to be measured. If the method or samples has some noise in it, it may be beneficial to have additional repetitions of the calibration measurements.

In another embodiment, the set number is two times the predetermined number of components plus one. Each exponential decay term has two calibration parameters. The number of variables in the calibration equation is then 2 times the number of exponential decay terms plus one. The two calibration parameters for the each exponential decay term are two variables that are contributed to the calibration equation. This embodiment may be beneficial because the number of samples is exactly the number needed to provide a solution to the calibration function. The number of calibration samples is fixed.

In another embodiment the set number is two times the predetermined number of components plus two, three, four or five. Each exponential decay term has two calibration parameters. In this embodiment the number of components is one, two, three, or four greater than what is necessary to provide a solution to the calibration function. This may provide for an efficient calibration with a limited number of additional measurements, which may be used to check for errors or to allow the use of a fitting algorithm.

In another embodiment, the set number is two times the predetermined number of components plus 2, 3, 4, 5, 6, 7, 8, 9, 10, 11, 12, 13, 14, or 15. Each exponential decay term has two calibration parameters. In this embodiment the number of components is greater than what is necessary to provide a solution to the calibration function. This may provide for an efficient calibration with a limited number of additional measurements, which may be used to check for errors or to allow the use of a fitting algorithm.

In another embodiment the calibration function has a number of calibration parameters. The set number is equal or larger than the number of calibration parameters. The calibration parameters as mentioned above are constants that can be adjusted in the calibration function.

In another embodiment the signal comprises any one of the following: an electrochemical measurement, a chemiluminescence measurement, a nephelometric measurement, a radioactive decay or radioactive count measurement, a photometric transmission measurement, a photometric scattering measurement, and combinations thereof.

In another embodiment the intensive property is a concentration of the analyte. In some examples the concentration may be a molecular concentration.

In another embodiment the analyzer comprises a photometric measurement module operable for measuring the signal wherein the signal is at least a portion of a photometric transmission spectra.

In another embodiment the molecular concentration is a molecular concentration of c-reactive protein. The predetermined number of components is 2. The predetermined number of components comprises first sized particles and second sized particles. The first sized particles are 130 nm (+/−20 nm) in diameter and are coated with murine monoclonal antibody. The second sized particles are 200 nm (+/−20 nm) and coated with different murine monoclonal antibodies. The particles are different in size and the affinities of the murine monoclonal antibodies in the two types are different by nature.

In another embodiment the analyzer is an automatic analyzer. An automatic analyzer as used herein is an analyzer that automates at least a portion of the process of analyzing the biological sample. This may include measurements and the recording of data. In other examples the automatic analyzer is operable for preparing the sample such as adding a solution or assay or even dilutant to the biological sample. In other embodiments the automatic analyzer may also be able to automatically load and unload different biological samples. For instance, the automatic analyzer may be operable for receiving the set of calibration samples and performing the calibration automatically without human intervention.

In another aspect, the disclosure provides for an automatic analyzer for analyzing the biological sample. The analyzer is operable for measuring a signal descriptive of an intensive property of an analyte in the biological sample using an assay. That is to say the assay is mixed in with the biological sample and then the analyzer measures the signal. In some examples the automatic analyzer may be operable for dispensing the assay automatically into the biological sample before making the measurement. The automatic analyzer is operable to receive the assay. The assay has a predetermined number of components. The predetermined number of components is greater than or equal to 2. Each of the predetermined number of components has a distinct relation between the intensive property and the signal. The automatic analyzer comprises a memory for storing machine-executable instructions. The automatic analyzer comprises a processor for controlling the automatic analyzer. Execution of the instructions causes the processor to receive a calibration. The calibration is defined by a calibration function equivalent to a constant plus an exponential decay for each of the predetermined components. Execution of the instructions further cause the processor to add the assay to the biological sample using the automatic analyzer. Execution of the instructions further cause the processor to measure the signal of the biological sample using the automatic analyzer. Execution of the instructions further causes the processor to calculate the physical property using the signal and the calibration.

In another embodiment, execution of the instructions further cause the processor to receive a set number of calibration samples with known values for the intensive property using the analyzer. Execution of the instructions further cause the processor to measure a calibration signal for each of the calibration samples using the analyzer and the assay. In some examples execution of the instructions may also cause the processor to dispense the assay into each of the calibration samples using the analyzer. Execution of the instructions further cause the processor to determine a calibration by fitting the calibration function to the calibration signal for each of the calibration samples and the known value for the intensive property. In some examples the set number is at least 2 times the predetermined number of components plus 1. Each of the exponential decay terms has two calibration parameters. Also in some examples the calibration function has a number of calibration parameters. The set number is equal to or greater than the number of calibration parameters.

In another embodiment, execution of the instructions further cause the processor to receive parameter information descriptive of the calibration. The parameter information may for instance be pre-measured calibration data, values for constants in the calibration function, and/or ranges of values for constants in the calibration function. For instance, the values or the range of values may be known for a particular lot or type of assay in advance. This may further reduce the number of calibration samples necessary to use. The parameter information may also be used in conjunction measured calibration signals to determine the calibration function.

In another embodiment the automatic analyzer comprises the assay.

In another embodiment the signal comprises any one of the following: an electrochemical measurement, a chemiluminescence measurement, a nephelometric measurement, a radioactive decay or counts, a photometric scattering measurement, a photometric transmission measurement, and combinations thereof.

In another embodiment the intensive property is a concentration.

In another embodiment the analyzer comprises a photometric measurement module operable for measuring the signal. The signal is at least a portion of the photometric transmission spectra.

In another embodiment the concentration is the concentration of c-reactive protein. The predetermined number of components is 2. The predetermined number of components comprises first sized particles and second sized particles. The first sized particles are approximately 130 nm in diameter and are coated with a murine monoclonal antibody. The second sized particles are approximately 220 nm and are coated with a different affinity murine monoclonal antibody.

Figure 1:
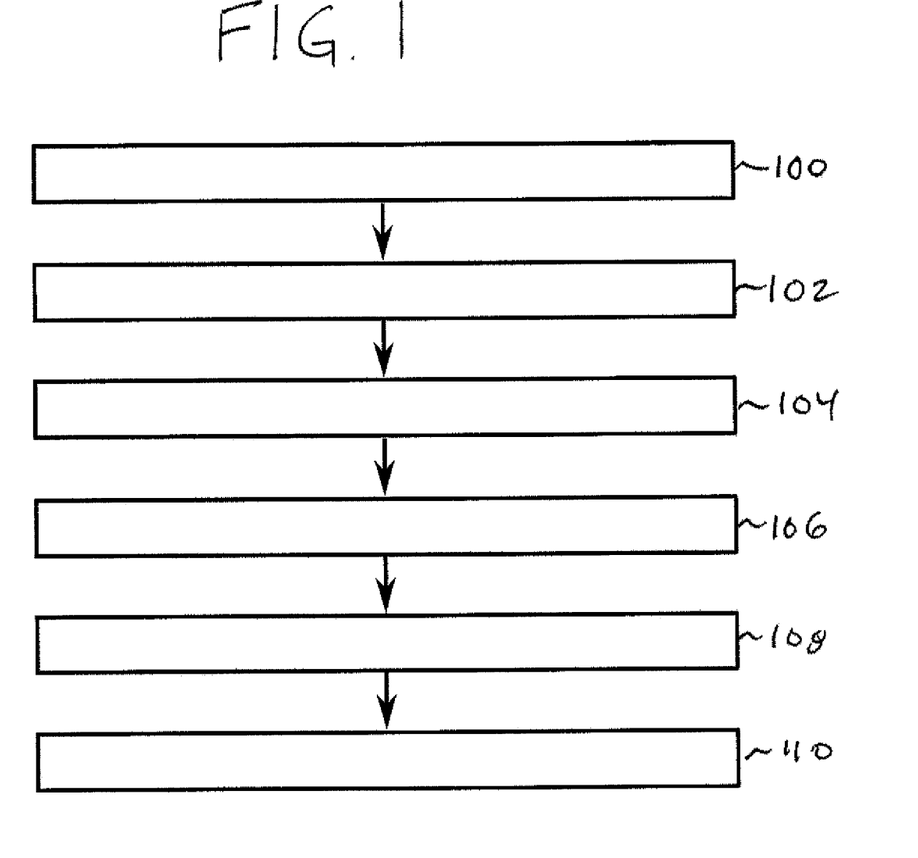
FIG. 1 illustrates an example of a method in accordance with an embodiment of the present disclosure.

FIG. 1 shows a flow diagram that illustrates an example of a method for analyzing the biological sample using an analyzer and an assay, in accordance with an embodiment of the present disclosure. The analyzer is operable for measuring a signal indicative of the intensive property of an analyte in the biological sample. In step 100 an assay is provided. The assay is operable to produce a signal. The assay may be operable to produce a signal when measured with the analyzer. The assay has a predetermined number of components. The predetermined number of components is > or = to 2. Each of the predetermined number of components has a distinct relation between the intensive property and the signal. Next, in step 102, a set of calibration samples is provided.

The calibration samples have known values for the intensive property. For instance, the calibration samples may have different concentrations of a particular compound or chemical. Next, in step 104, a calibration signal is measured for each of the calibration samples using the analyzer and the assay. For instance, the assay may be dispensed into each of the calibration samples. Next, in step 106, a calibration is determined by fitting a calibration function to the calibration signal for each of the calibration samples and the known values for the intensive property. The calibration function is equivalent to a constant plus an exponential decay term for each of the predetermined number of components. Next, in step 108, the signal of the biological sample is measured using the analyzer and the assay. Finally, in step 110, the intensive property is calculated using the signal and the calibration.

Figure 2:
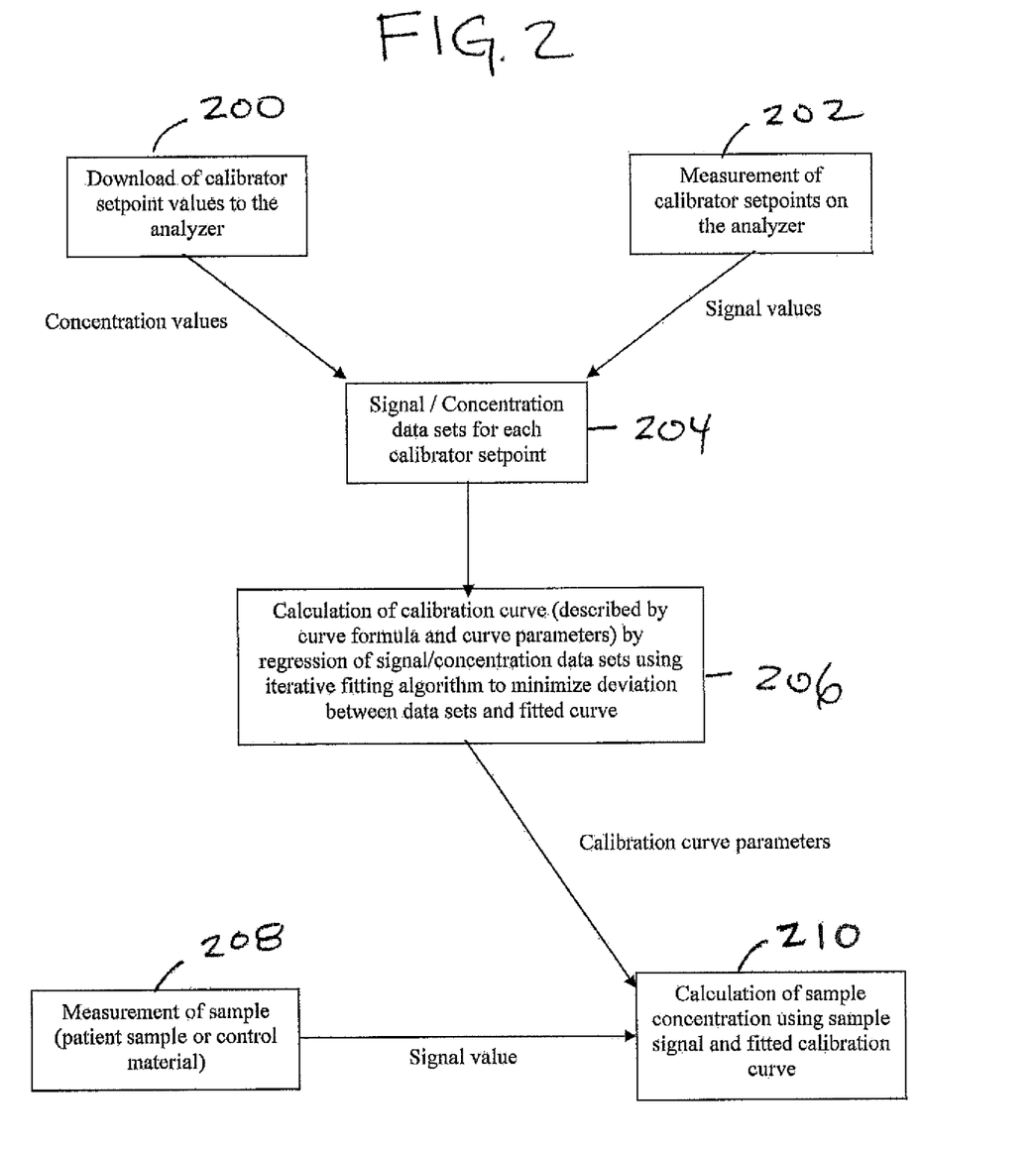
FIG. 2 illustrates a further example of a method in accordance with an embodiment of the present disclosure.

FIG. 2 shows another example of a method of analyzing a biological sample using an analyzer and an assay, in accordance with an embodiment of the present disclosure. In the example in FIG. 2, first a calibration is performed and then the calibration is used for determination of a physical property or intensive property of an analyte. In step 200 calibrator set point values are downloaded to an analyzer. These are equivalent to the known values for the intensive property. In step 202, the measurement of the calibrator set points is performed using the analyzer. This provides signal values. The signal values are equivalent to the calibration signals for each of the calibration samples. Then, in step 204, the concentration values and signal values provide a dataset for each calibrator set point. Next, in step 206, the calibration curve is calculated. This in some examples may be described by the curve formula and the curve parameters. The curve formula and curve parameters is the calibration function. The curve parameters are the calibration parameters or the constants that are varied in the calibration function. This calculation of the calibration may for instance be performed by regression of the signal and concentration datasets using an iterative fitting algorithm to minimize deviation between the datasets and the fitted curve. This may be performed in a variety of ways. For example, a least squared fitting method may be employed. If the number of the data points of signal and concentration is equal to 2× the predetermined number of components+1, then the parameters of the calibration curve can be solved. Step 206 provides a calibration function or a calibration curve with parameters. Next, in step 208, a sample is measured using the analyzer. This for instance may be a patient sample or some sort of control material for checking the calibration. This provides a signal value or signal. In step 210, the calculation of the sample concentration or intensive property is performed using the sample signal and a fitted calibration curve.

Figure 3:
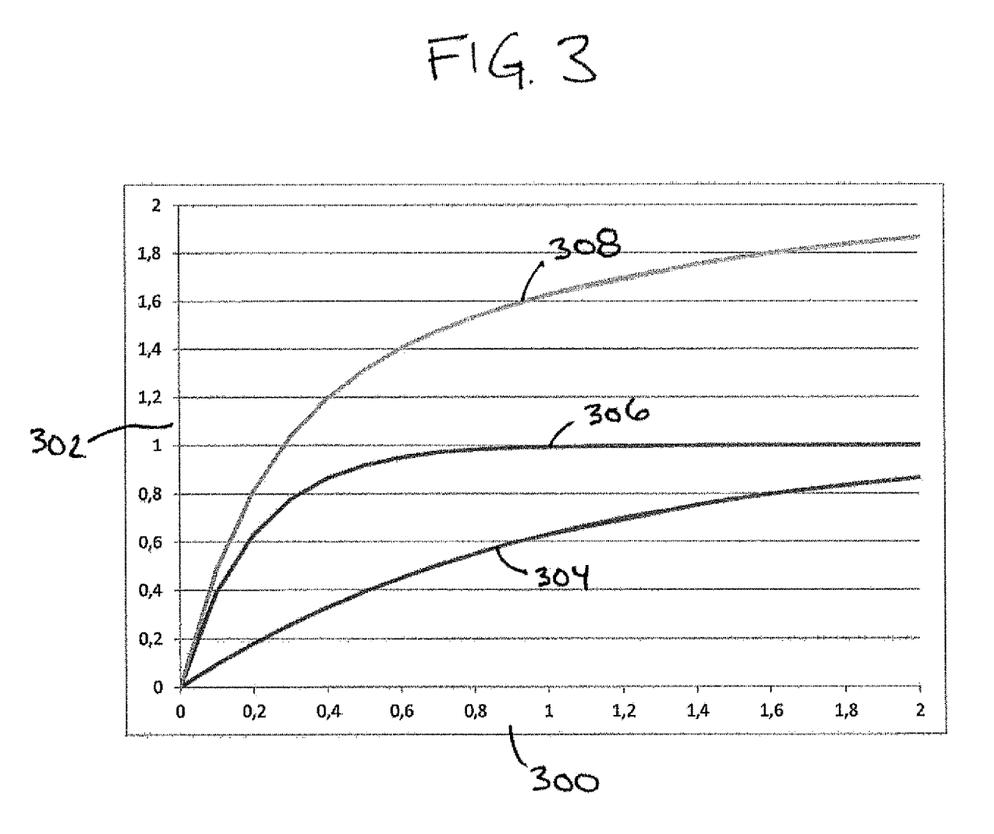
FIG. 3 illustrates the combination of several exponential decay functions in accordance with an embodiment of the present disclosure.

FIG. 3 shows a plot of several functions, which is in accordance with an embodiment of the present disclosure. The x-axis 300 is in arbitrary units and the y-axis 302 is also in arbitrary units. The function 304 plots the value of the curve of 1−e raised to the −x. Function 304 is an example of an exponential decay term. The curve 306 is the function 1−e raised to the −5x. Curve 306 illustrates another example of an exponential decay function. The curve 308 is the sum of curves 304+306. It can be noted that upon examination the curve 308 looks similar in form to an exponential decay term. When performing a calibration one may actually try to fit an exponential decay term to the curve 308 by itself. However, because of the sum of curves 304 and 306 the fit would be mediocre at best. FIG. 3 illustrates how when there are multiple components that both contribute to the same signal 308, the embodiment of the disclosure may provide for an improved means of fitting a calibration curve.

Figure 4:
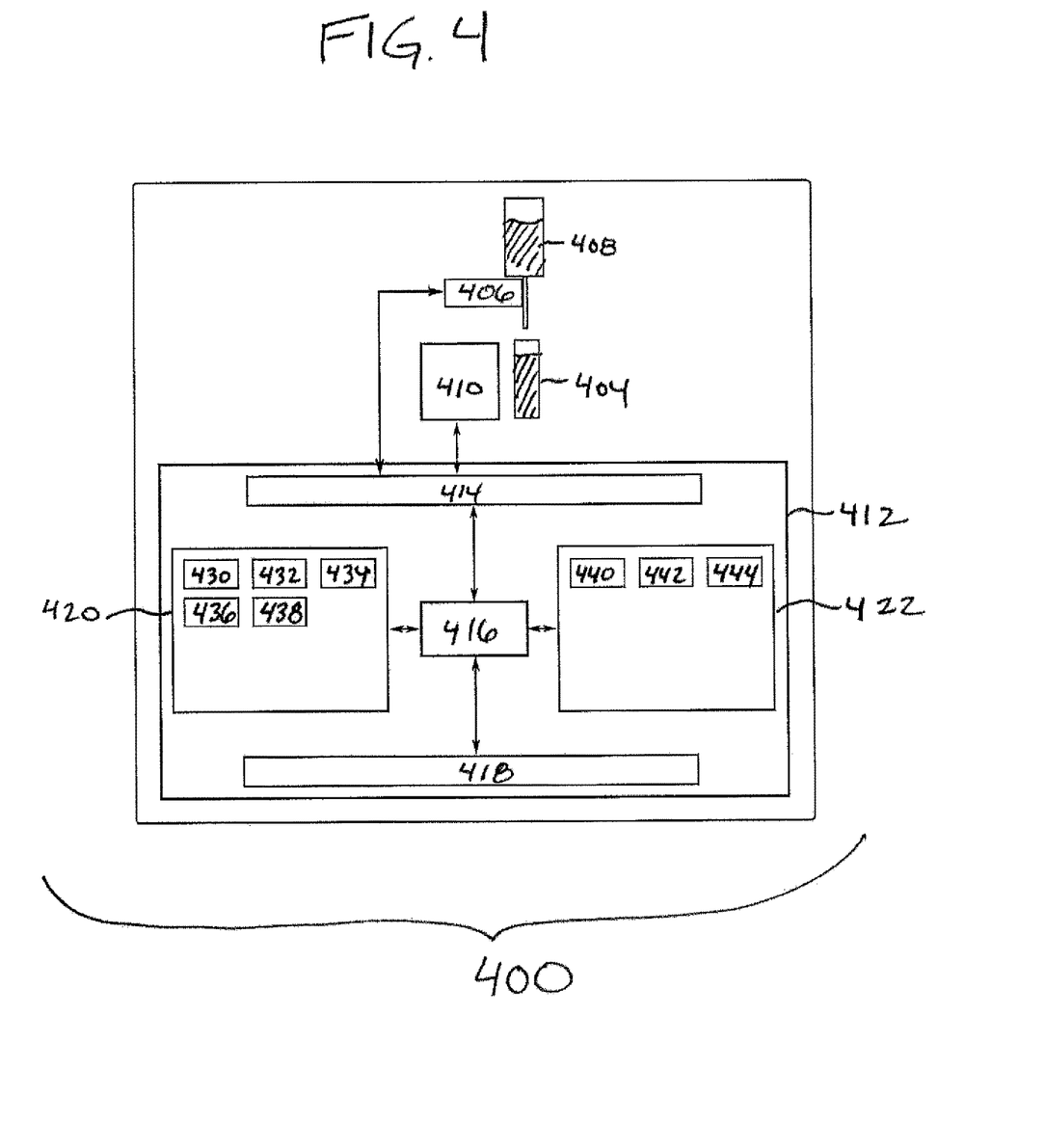
FIG. 4 illustrates an example of an automatic analyzer in accordance with an embodiment of the present disclosure.

FIG. 4 shows an example of an automatic analyzer 400, in accordance with an embodiment of the present disclosure. The automatic analyzer 400 is operable for analyzing a biological sample 404. There is a dispenser 406 that is operable for dispensing an assay 408 into a biological sample 404. The biological sample comprises an analyte. The assay 408 may for instance be located within a cartridge. The assay 408 comprises at least two components that are also assays.

Although not shown in this FIG. 4, the automatic analyzer 400 may have an apparatus for positioning multiple biological samples 404 for dispensing the analyte and also for being analyzed by a measurement module 410. The measurement module 410 is representative of many different types of sensors or instruments that are capable of making measurements on a biological sample 404.

The dispenser 406 and the measurement module 410 are connected to a hardware interface 414 of a computer system 412. The computer 412 further comprises a processor 416, which is in connection with the hardware interface 414, a user interface 418, computer storage 420 and computer memory 422.

The computer storage 420 is shown as containing values 430 for the intensive properties of calibration samples. The computer storage 420 is further shown as containing calibration signals for the calibration samples 432. The computer storage 420 is further shown as containing a calibration 434, which has been calculated using the values 430 and the calibration signals 432. The computer storage 420 is further showing the signal 436 of a biological sample 404 that has been measured by the measurement module 410. The computer storage 420 is further shown as containing a value 438 of an intensive property calculated using the signal 436 and the calibration 434.

The computer memory 422 is shown as containing a control module 440. The control module 440 comprises computer-executable code that enables the processor 416 to control the operation and function of the automatic analyzer 400. For instance, it enables the processor 416 to send commands via the hardware interface 414 and receive information from the dispenser 406 and the measurement module 410. If they are present, this module also enables the processor 416 to control automatic routing and processing of the biological sample 404. The computer memory 422 is further shown as containing a curve fitting module 442. The curve fitting module 442 contains computer-executable code that enables the processor 416 to calculate the calibration 434 using the calibration signals 432 and the values 430. The computer memory 422 is further shown as containing an intensive property determination module 444. The module 444 uses the calibration 434 and the signal 436 to calculate the value 438.

In order that the embodiments of the present disclosure may be more readily understood, reference is made to the following examples, which are intended to illustrate the invention, but not limit the scope thereof.

In some examples the known calibration curves may not match the shape of the calibration curve well. In this case often the spline model, either linear or a cubic spline, is used. However, the use of a spline may require a large number of calibration measurements. Examples of the calibration function may be applied to the so called CRP test. CRP is an abbreviation for c-reactive protein. The c-reactive proteins are proteins found in the blood, which have their levels rise in response to an inflammation. The CRP is a classic acute phase protein to inflammatory reactions. It is synthesized by the liver and consists of five identical polypeptide chains that form a five-membered ring having a molecular weight of 120,000 Daltons. CRP is the most sensitive of the acute phase reactants and its concentration increases rapidly during the inflammation processes. Healthy persons will typically have only a very low concentration of c-reactive protein in their blood. Reference values according to IFCC/ERM protein standardization are less than 5 mg per liter. During acute inflammation processes the CRP concentrations in serum and/or plasma can increase up to 1000 fold. The CRP assay therefore faces two challenges. The low serum concentrations of CRP of obviously healthy people, especially around the decision range of 5 mg per liter should be measured with high accuracy and sensitivity as well as the assay should be able to detect high serum concentrations of CRP patients with acute inflammatory processes without too high re-run rates. Some CRP assays are able to detect CRP without re-runs within the concentration range of 0.3 mg per liter and 350 mg per liter. This can be achieved by the help of two different microparticles (DuRel). A small sized particle of approximately 130 nm size, coated with low affinity CRP MaB and a larger sized particle of approximately 220 nm coated with a high affinity CRP MaB. The combination of those two particle types in one reagent leads to an overlap of the binding curves or calibration curves. A sharp increase of the signal at low CRP concentrations induced by the large particles is combined with a moderate increase of the signal at higher concentrations, induced by the small particles. The dose signal curve is a combination of the two binding curves and its shape is not typical for latex-based turbidimetric assays. The six available set-points have to be distributed in the majority of a lower concentration range of the calibration curve, four points between 0 and 9 mg per liter, two between 90 and 350 mg per liter, in order to achieve the necessary accuracy in a lower concentration range. The fitting of the resultant calibration curves with standard calibration functions is a problem that has not been solved with the accuracy needed to date. Most of the nonlinear calibration functions do not meet the set points adequately. Therefore they are not suitable because the accuracy at the medical decision point is insufficient. Actually a linear model is not suitable to cover the full measuring range between 0.3 and 350 mg per liter. Even the aforementioned nonlinear Rodbard model is not able to provide sufficiently accurate fits especially in the medical decision range, approximately 5 mg per liter.

So far the current state of the art has been to fit a spline function. However, as has been discussed already, the spline function involves disadvantages with regards to robustness and accuracy. Examples may provide a new method of calibrating diagnostic tests using a new calibration curve. For the CRP test using two particle sizes a five parameter model function may be used.

At the early beginning of assay calibration history, curve fitting was restricted to simple straight lines. The fitting is easy and has always been one best parameter set. Often great effort was necessary to get the chemical reaction linear in the target range. With increasing requirements for the measurement range this approach was limited very early. Another approach is the use of local models, for example the spline. Especially splines involving higher order terms fit the measurement perfect but do not maintain a stable overall curve nor accommodate for measurement error.

The next generation of calibration curves are nonlinear sigmoidal curves. They originate from dose-response theory that were introduced to model enzymatic reactions by Rodbard. These models are state of the art and are available at nearly all analyzers on the market. They model the reaction of a given reagent with the analyte within the human specimen. These models work well for very many immunological assays and allowed to broaden measurement ranges very significantly. With further increase of the requirements especially with respect to the measurement range more complex assay formats are needed. Eventually multiple superimposed reaction flows help to account for the enhanced requirements. The classic sigmoidal model, classic one reaction mode is not up to the mark of new types of multiple superimposed reactions with sufficient performance. The idea of superimposed reactions on the chemical side needs an appropriate answer on the mathematical side. Starting from basic kinetics the super-position idea was analyzed and transferred in a very systematic way to fulfill the new requirements met.

A key point is the strategy for the selection and the evaluation of the mathematical model. While the selection is more or less straight forward: any nonlinear analytical, small parameter number of scalar function capable to model smooth monotonous curves is a valid candidate. The evaluation of the new function of the algorithm is a complex process. To get all relevant steps as clear as possible it makes sense to refer to the final solution: at the very end we want to have only a few calibrators 4-5 to model the relationship between the concentration and signal without bias and variability due to calibration. This should hold true for the whole measurement range and especially the area where the outcome is clinically critical.

At the start the complete and true relationship between signal and concentration needs to be established. This is done by a large set of calibrators, for example more than ten, which cover the whole measurement range. The data should cover several devices, and include several runs to account for possible measurement system and reagent fluctuations. Furthermore, automatic and manual preparations of the calibrators, dilution, by several operators should be involved if appropriate as well. On this basis one or multiple, for example system-specific, typical curves can be established.

The next step is to search for a suitable function that is capable to adequately describe the signal-to-concentration relationship. However, the mathematical function is only half the story. Nonlinear optimization can be done following different approaches. Basically in the parameter fitting a quadratic form is minimized. At the end of the day an optimization algorithm finally leads to a final set of parameters for the selected calibration function. Different optimization strategy algorithms like the "Nelder-Mead," "Taylor," "Levenberg-Marquardt" or simulated annealing were examined.

Starting with many calibrators, for example more than 10, the shape of the curve is fixed well and the fitted curve can be verified easily by checking the closeness of agreement between data and curve on a large and well-defined set of calibration curve data. Once good solutions have been identified for the large calibrator set it has to be shown that the mathematical model and the fitting procedure works for the routine with 4-5 calibrators as well. The goal here is to demonstrate that there is no loss of fit quality when we move from 20 to 5 calibrators. A criterion to evaluate the candidate models are the residuals as well as the overall deviation of a 5 calibrator solution from the original n, n>10 calibrator solution.

A further strategy for the evaluation of potential candidate solutions rests on simulations. Starting from a curve given by the parameters it is possible to read points from the curve at a typical concentration position we know from the calibrators. Then we add to the signal some typical noise that we expect from the analysis of measurement errors. This can be repeated within simulations and helps to identify concentration ranges where the fit may be biased, that is, the curve deviates away in the same direction. This analysis assures that the chosen models is neither locally biased nor the robustness with regard to measurement fluctuations is insufficient.

The data variability from practical measurements is difficult to be fully captured by simulations since selected function in the algorithm typically demonstrate with real world data a certain amount of robustness. To examine robustness, simulation again is a method of choice. We start again as described above, but now we increase the size of the noise that has added to the signal. If the noise exceeds certain levels we may observe more and more failing fits. This illustrates very easily the robustness in the field.

Further, by generating the random noise two different error models are available. The model of statistically independent error is a very conservative and robust variant, because the noise of different calibrators is not correlated. The second mode uses the real correlation of errors by analyzing the signals from a set, >10, of different calibration curves. The last method allows real predictions to the performance and the first model means increased strength for the algorithm.

A concrete example of a calibration formula that is robust is Equation 1, which may be used with the previously discussed CRP assay.

Examples of the calibration function may have the advantage of providing a valid calibration over a large measurement range and also to discriminate between measurement and model error. To meet demanding medical requirements in assay design the detection process can be different biochemical processes. So, for example, in the CRP assay, latex-particles of different sizes are involved in the same assay formulation to detect low and high concentrations of CRP, respectively. This design leads to assay calibration curves that are different in the different concentration regimes and constitute a challenge for the classical one-detection process modeling mathematical functions used in nonlinear calibrations. As a consequence, these assays are often fitted by spline functions, which have well-known inherent disadvantages. In particular, as for the spline model no global function exists for calibrating the whole measurement range, and no distinction between measurement error and model error in the calibrator signal can be made. Error detection procedures that could be implemented with the nonlinear global model approach are not feasible for the spline model. Examples may use specifically designed nonlinear mathematical functions that allow for excellent model-based fit of the whole measurement, thereby covering multiple detection processes. For the particular examples of the CRP assay, which is based on two sizes of latex-particles and uses two detection processes in the same assay formulation, it has been shown that specific superposition of two exponential decay functions allows for a perfect fit of the calibration curve, which is composed of a curve and a more or less straight section.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. An automatic analyzer for analyzing a biological sample, comprising:
    an assay apparatus operable to measure an intensive property of an analyte in a biological sample and generate a signal descriptive of the intensive property of the analyte, wherein the intensive property is a concentration of the analyte and wherein the analyte is C-reactive protein (CRP), the assay apparatus comprising an assay reagent having a predetermined number of at least two components, each having distinct particle sizes and each having a distinct relation between the concentration of CRP and the generated signal, wherein each of the predetermined number of components is a distinct assay;
    a dispenser, for dispensing the assay reagent into the biological sample comprising the CRP;
    a photometric measurement instrument configured to measure the generated signal, wherein the signal is within at least a portion of a photometric transmission spectra;
    a computer comprising:
        a hardware interface in communication with the dispenser and the photometric measurement instrument;
        a memory encoded with a control module comprising computer-executable code for controlling the operation and function of the automatic analyzer when executed; and
        a processor in communication with at least the hardware interface, and the memory, the processor configured to execute the computer-executable code of the control module, wherein the execution of the computer-executable code causes the processor to:
            receive a set number of calibration samples with known values for the concentration of CRP using the analyzer and/or receive parameter information descriptive of a calibration, wherein the set number is two times the predetermined number of components plus one, two, three, four or five;
            measure a calibration signal for each of the calibration samples using the analyzer and the assay reagent;
            determine the calibration by fitting a calibration function to the calibration signal for each of the calibration samples and the known CRP concentration values; wherein the calibration function is equivalent to a constant plus an exponential decay for each of the predetermined components, wherein the calibration function includes a sum of two exponential decay terms, wherein each exponential decay term has two calibration parameters;
            add the assay reagent to the biological sample using the automatic analyzer;
            measure the generated signal of the biological sample using the automatic analyzer; and
            calculate the concentration of CRP in the biological sample based on the generated signal and the calibration.

2. The automatic analyzer of claim 1, wherein the signal further comprises any one of the following: an electrochemical measurement, a chemiluminescence measurement, a nephelometric measurement, a radioactive decay measurement, a photometric scattering measurement, and combinations thereof.

3. The automatic analyzer of claim 1, wherein the concentration of c-reactive protein is a molecular concentration of c-reactive protein, wherein the predetermined number of components is two, wherein the predetermined components comprises first sized particles and second sized particles, wherein the first sized particles are approximately 130 nm in diameter and are coated with a murine monoclonal antibody, and wherein the second sized particles are approximately 220 nm and coated with a different affinity murine monoclonal antibody.

4. The automatic analyzer of claim 1, wherein the set number is at least two times the predetermined number of components, plus one.

5. The automatic analyzer of claim 4, wherein the set number is two times the number of exponential decay terms, plus one.

6. The automatic analyzer of claim 1, wherein the calibration function has a number of calibration parameters, and wherein the set number is equal or larger than the number of calibration parameters.

7. The automatic analyzer of claim 1, wherein the automatic analyzer is configured to automatically load and unload biological samples.

8. The automatic analyzer of claim 1, wherein the automatic analyzer is configured to automatically receive the set of calibration samples and automatically perform the calibration without human intervention.

9. The automatic analyzer of claim 1, wherein the automatic analyzer is configured to automatically prepare the biological sample by automatically adding at least one of a solution or a dilutant to the biological sample.

10. The automatic analyzer of claim 1, wherein the automatic analyzer is configured to automatically prepare the biological sample by automatically adding the assay reagent to the biological sample.

* * * * *